United States Patent [19]
Fitton

[11] Patent Number: 6,106,771
[45] Date of Patent: Aug. 22, 2000

[54] SYSTEM AND METHOD FOR DESCALING AND DISINFECTING DENTAL WATERLINES

[76] Inventor: Russell P. Fitton, 820 S. Northwest Hwy., Barrington, Ill. 60010

[21] Appl. No.: 09/075,871
[22] Filed: May 11, 1998
[51] Int. Cl.[7] ....................................................... A61L 2/18
[52] U.S. Cl. .................................. 422/14; 422/7; 422/28; 422/292; 210/764; 134/26; 134/28; 134/95.1; 134/166 C; 433/229
[58] Field of Search .................................. 422/7, 14, 28, 422/40, 292; 210/764; 134/26, 28, 95.1, 166 C; 433/229

[56] References Cited

U.S. PATENT DOCUMENTS

| 4,545,956 | 10/1985 | Ciszewski et al. | 422/28 |
| 4,647,458 | 3/1987 | Ueno et al. | 422/28 |
| 4,752,444 | 6/1988 | Bowen et al. | 422/28 |
| 4,847,088 | 7/1989 | Blank | 424/404 |
| 5,055,043 | 10/1991 | Weiss et al. | 433/86 |
| 5,109,880 | 5/1992 | Booth | 134/108 |
| 5,158,454 | 10/1992 | Viebahn et al. | 433/82 |
| 5,324,477 | 6/1994 | Schroeder et al. | 422/37 |
| 5,526,841 | 6/1996 | Detsch et al. | 134/95.1 |
| 5,587,146 | 12/1996 | Wood et al. | 424/49 |
| 5,709,546 | 1/1998 | Waggoner | 433/82 |
| 5,731,275 | 3/1998 | Prevost et al. | 510/161 |
| 5,837,204 | 11/1998 | Prevost et al. | 134/166 C |

OTHER PUBLICATIONS

Christensen et al., "Dental Unit Waterlines: Is This One of Dentistry's Compelling Problems?" *Dentistry Today*, pp. 80–87, Jan. 1998.

J.F. Williams et al., "Microbial Contamination of Dental Unit Waterlines: Prevalence, Intensity and Michrobiological Characteristics," *Journal of the American Dental Asosication*, vol. 124, No. 10, 1993. pp. 59–65.

B.G. Shearer, "Biofilm and the Dental Office," *Journal of the American Dental Asosication*, vol. 127, No. 2, 1996. pp. 181–189.

Center for Disease Control and Prevention: Recommended Infection–Control Practices for Dentistry, 1993, *MMWR* 42:No. RR–8, 1993, pp. 1–12.

*Primary Examiner*—Robert J. Warden, Sr.
*Assistant Examiner*—Fariborz Moazzam
*Attorney, Agent, or Firm*—Brinks Hofer Gilson & Lione

[57] ABSTRACT

A portable system and method for softening and disinfecting dental waterlines is disclosed. The portable system and method combines a routing valve, a water supply, and a portable device capable of delivering a descaling and an anti-microbial agent. The routing valve has an inlet and an outlet. The outlet is attached to a water supply line of sufficient volume to deliver water throughout the system. The inlet is attached to a portable device capable of delivering a descaling agent and an anti-microbial agent.

17 Claims, 2 Drawing Sheets

SYSTEM AND METHOD FOR DESCALING AND DISINFECTING DENTAL WATERLINES

BACKGROUND OF THE INVENTION

The present disclosure relates to delivering water of optimal microbiologic quality, and more particularly to a portable system, device, and method that neutralizes calcium, magnesium, and pathogenic contaminants in dental waterlines.

All sources of water possess naturally occurring contaminants. As water is a universal solvent, many minerals and pathogenic microorganisms directly contaminate water supplies. Low level exposure to these contaminants pose little risk to water quality and their removal does not always provide greater health protection. However, documented outbreaks of waterborne disease and reports of waterborne infection from municipal water supplies illustrate the growing threat of contaminated drinking water.

The standard of dental care concerning infection control has long focused on hygienic practices including the effective sterilization of dental handpieces, turbines, water syringes, and intraoral devices. In the past, dental waterlines were frequently overlooked when planning effective infection control. As there were few reported adverse health effects to dental water exposure, there was little evidence of a public health risk. In 1993, the Centers for Disease Control and Prevention (CDC) recognized the microbiologic quality of water used in dental treatment could be improved. Accordingly, the CDC recommended a number of infection control practices to be followed in dental operatories. A routine practice of flushing waterlines continuously at the beginning of each clinical day was recommended to substantially reduce microbial accumulations. Sterile saline and sterile water purges were also recommended practices. However, active adhesion of pathogenetic microorganisms to polyvinylchloride and the inadequate maintenance of sterile saline and sterile water supplies allow some pathogens to survive in spite of these preventive practices.

A commonly followed practice for controlling waterline contamination in dental units has been to install independent water systems. These systems allow delivery of sterile water effectively eliminating the threat of municipal water microcontamination. Dental waterlines, however, have shown that heterotrophic bacteria, fungi, and protozoans can survive in sterile water. The colonization and replication of these microorganisms result in microbial accumulations, known as biofilms. Prolonged exposure to the interior surfaces of waterlines result in adhesion, microbial multiplication, and ensuing colonization. Biofilms are generally asymmetrically distributed and are known to associate in microcolonies. Some systems attempt to eliminate biofilm colonies by improving the water supplied to dental unit. These systems are not always effective because once biofilms form they reproduce.

Scale buildup occurs when dissolved minerals suspended in water precipitate or fall out of their suspended state. The storing of water in dental units can cause scale buildup which is a concentration of calcium and magnesium attaching to waterlines, fittings, valves, and sensors. Calcium and magnesium scales reduce the cleaning and disinfecting performance of many germicidal agents thereby requiring the use of stronger chemical mixtures to attain uncertain results. To that end, hard water left untreated may cost practitioners higher operating costs, restricted water flow, reduced water pressure, and poor water quality even when an aggressive water quality control program is followed.

Practitioners following conventional practice may install water softeners that remove calcium and magnesium minerals from water to their disinfecting systems. For every calcium and magnesium ion removed, conventional water softeners add two salt ions which do not interfere with the disinfecting process. Softened water, however, is not always recommended for consumption and therefore, secondary systems such as filtration systems may be needed to remove sodium or other harmful media as part of the unique nature of patient care. The addition of a filtration system further increases the cost and maintenance of conventional disinfecting systems and may provide a breeding surface for bacteria if not properly maintained.

Another practice for controlling waterline contamination in dental units is the use of micro-filtration systems exclusively. These systems attempt to suppress bacterial contaminants by filtering water primarily at a point-of-entry to the dental unit. The filters, however, do not treat waterlines up and to the waters point-of-use and like conventional filters may provide a breeding surface for biofilm growth.

In other conventional systems, the dental waterlines are periodically or continuously flushed with a disinfecting agent. These processes do not always eliminate bacterial contamination as scale, may isolate the disinfectant allowing subsequent waterline contamination, and create an environment that promotes bacterial resistance to the disinfectant. A periodic or continuous use of the disinfectant, therefore, may pose a risk to the dental patient if all contamination including scale deposit is not first removed.

As the focus shifts to reducing the risk of disease transmissions in all aspects of dental practice, an effective infection control system for decontaminating dental waterlines is needed. As the ADA expressed in its Dec. 13, 1995, Statement on Dental Waterlines, there is a need to improve dental waterline quality.

SUMMARY OF THE INVENTION

A portable system and method for softening and disinfecting dental waterlines is disclosed. The portable system and method combines a routing valve, a water supply, and a portable device capable of delivering a descaling and an anti-microbial agent. The routing valve has an inlet and an outlet. The outlet is attached to a water supply line of sufficient volume to deliver water throughout the system. The inlet is attached to a portable device capable of delivering a descaling agent and an anti-microbial agent.

DETAILED DESCRIPTION OF THE PRESENTLY PREFERRED EMBODIMENTS

The present disclosure departs from conventional art in its functional integration and portability. In an embodiment of the invention, a means for defining a portable reservoir is a cylindrical tank or any other fully portable enclosed reservoir. The cylindrical tank preferably has an inlet to receive fluids and an outlet line to deliver descaling and antimicrobial agents. A pump provides a means for moving the descaling and anti-microbial agents from the cylindrical tank through a plurality of dental waterlines. The use of releasable connectors which are means for connecting the cylindrical tank's outlet line to a dental unit conveniently allows quick connections and use with little set-up time.

Figure 1:
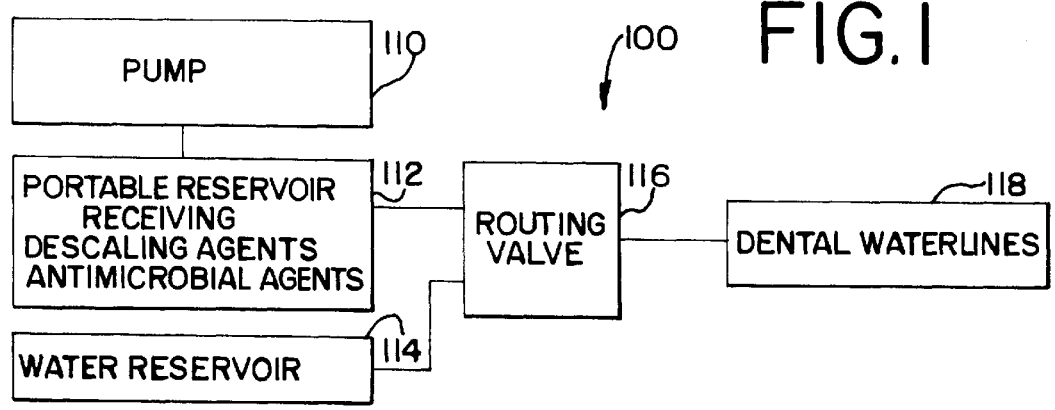
FIG. 1 is a schematic illustration of a first embodiment of the descaling and disinfecting system.

As shown in FIG. 1, a descaling and disinfecting system 100 is illustrated. A pump 110 is connected to a portable reservoir 112 preferably adapted to receive descaling and anti-microbial agents. An outlet line extending from the portable reservoir 112 provides a fluid flow path from the portable reservoir 112 to a first inlet of a routing valve 116. A second inlet of the routing valve 116 is connected to a water reservoir 114. Routing valve 116 also incorporates a flow controlling valve for selecting between the portable reservoir 112 and the water reservoir 114. Routing valve 116, further incorporates a quick disconnect coupling at its first inlet. The quick disconnect coupling is of any suitable type that is capable of releasably engaging and disengaging the outlet line extending from the portable reservoir 112. In order to prevent fluid flow from the inlets, a check valve is enclosed in the routing valve 116. The check valve is biased to a closed position to seal the inlets when the inlets are not engaged.

In typical practice, descaling or anti-microbial agents are impelled from the reservoir 112 by the pump 110. The pump 110 is typically a manual pump, although electrical, pneumatic or other activated pumps, whether they be driven by a transportable or a fixed power source, may be used.

Operation of the of dental softening and disinfecting system is best understood by a step-by-step illustration of the four-cycle process. In typical operation, the outlet line of the portable reservoir 112 is releasably coupled to the routing valve 116. A descaling agent contained in the portable reservoir 112 is circulated through the dental waterlines 118 by operation of the pump 110. An important feature of the routing valve 116 is its ability to shut-off water flow while an agent is circulated through the waterlines 118. In recognizing the condition of the waterlines 118, the descaling agent is retained in the waterlines 118 for a sufficient period of time to remove scale deposits. The waterlines 118 are then flushed and drained while the portable reservoir 112 is filled with an anti-microbial agent. The anti-microbial agent is then delivered to the waterlines by engaging the manual pump 110. In normal practice, the anti-microbial agent remains in the lines for sufficient time to disinfect the waterlines 118. The process is completed when the waterlines 118 are again flushed and the portable reservoir 112 outlet line is releasably disconnected from the routing valve 116.

When the dental descaling and disinfecting system 100 is employed improved results are achieved. In accordance with this process, water samples were analyzed using a standard spread plate method. Before the waterlines were treated, water sampled at three different outlets were found to contain between 580 and 25,600 Colony Forming Units (CFU) per milliliter of water. After the process was employed no CFU growth was detected in two samples and less than 100 CFU per milliliter of water were found in the remaining sample.

Figure 3:
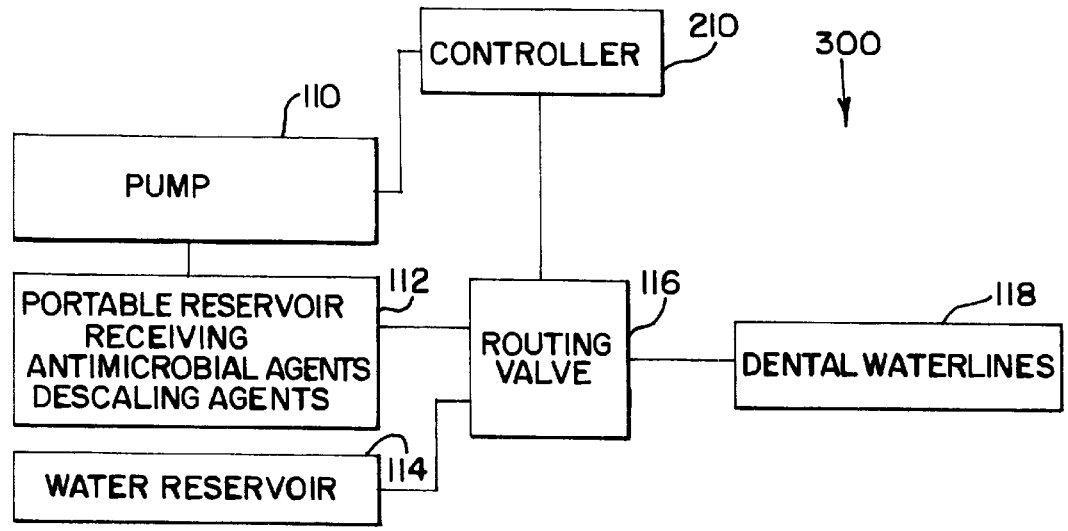
FIG. 3 is a schematic illustration of a second embodiment of the descaling and disinfecting system.

FIG. 3 illustrates a similar embodiment to that depicted in FIG. 1. As shown, the descaling and disinfecting system 300 comprises a portable reservoir 112, a pump 110, a water reservoir 114, and a routing valve 116. However, in this embodiment a controller 210 is a part of the softening and disinfecting system 100. The controller 210, preferably is a programmable microprocessor capable of managing the four-cycle process described above. The microprocessor may be interfaced to the routing valve 116, the pump 110, and a waterline drain to fully automate the treatment process. The controller 210 may allow time-delayed treatment from the portable system 100 without operator involvement.

It is further envisioned that the portable reservoir 112 may be divided into separate chambers. A first chamber may be adapted to receive a descaling agent and a second chamber may be adapted to receive an anti-microbial agent.

Figure 4:
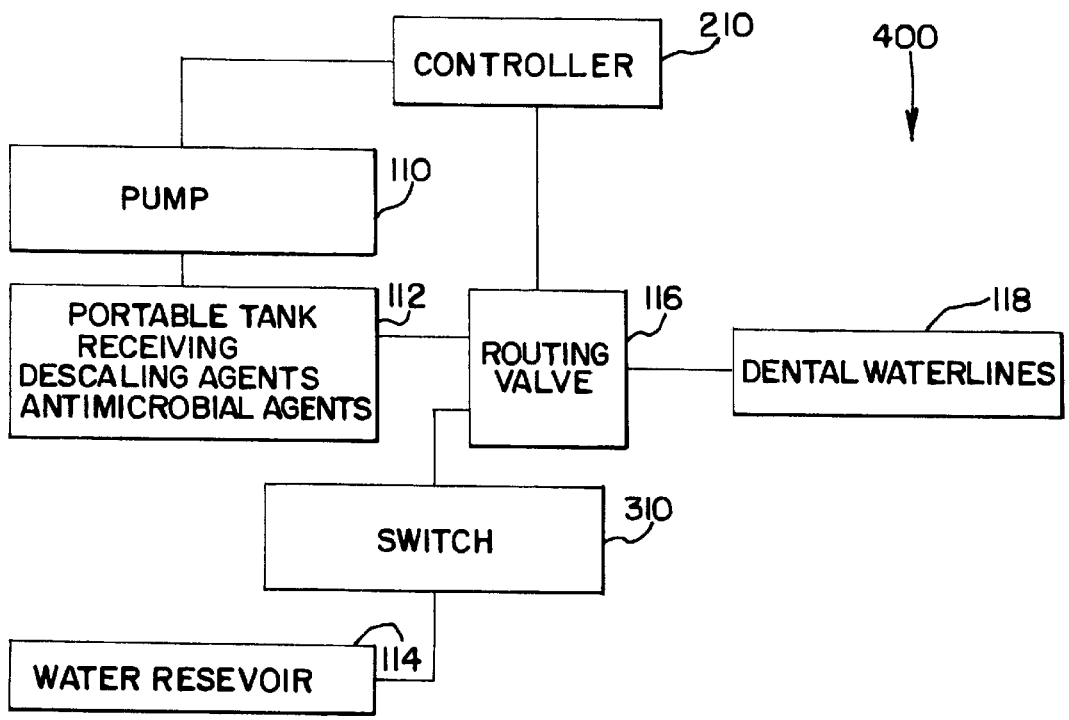
FIG. 4 is a schematic illustration of a third embodiment of the descaling and disinfecting system.

FIG. 4 illustrates a third embodiment of the dental softening and disinfecting system 400. A switch 310 may be employed to shut-off the water flow from the system. In practice, the water flow switch 310 may be employed in any embodiment described herein.

In addition to the above features, the descaling and disinfecting system may further comprise a pH sensor (or similar device) to measure the acidic or alkaline qualities of the water reservoir. The sensor may function with the controller 210 and a visual or audio display to provide an indication of water quality. For example, an acidic condition may correlate to high concentration of pathogenic contamination. Additional features may include: flow sensors, pressure gauges, and programmable alarms that alert practitioners to contamination.

Individuals skilled in the art will appreciate the wide array of descaling and anti-microbial agents that may be used in the aforementioned embodiments. For instance, lactic, tartaric, acetic, citric, ascorbic, malic, succinic, gluconic, fumaric, and phytic acids in combination with phosphoric, nitric, sulfuric, or hydrochloric acid, and alcohol are effective anti-microbial agents, among others. Likewise, vinegar is one of many effective descaling agents.

Figure 2:
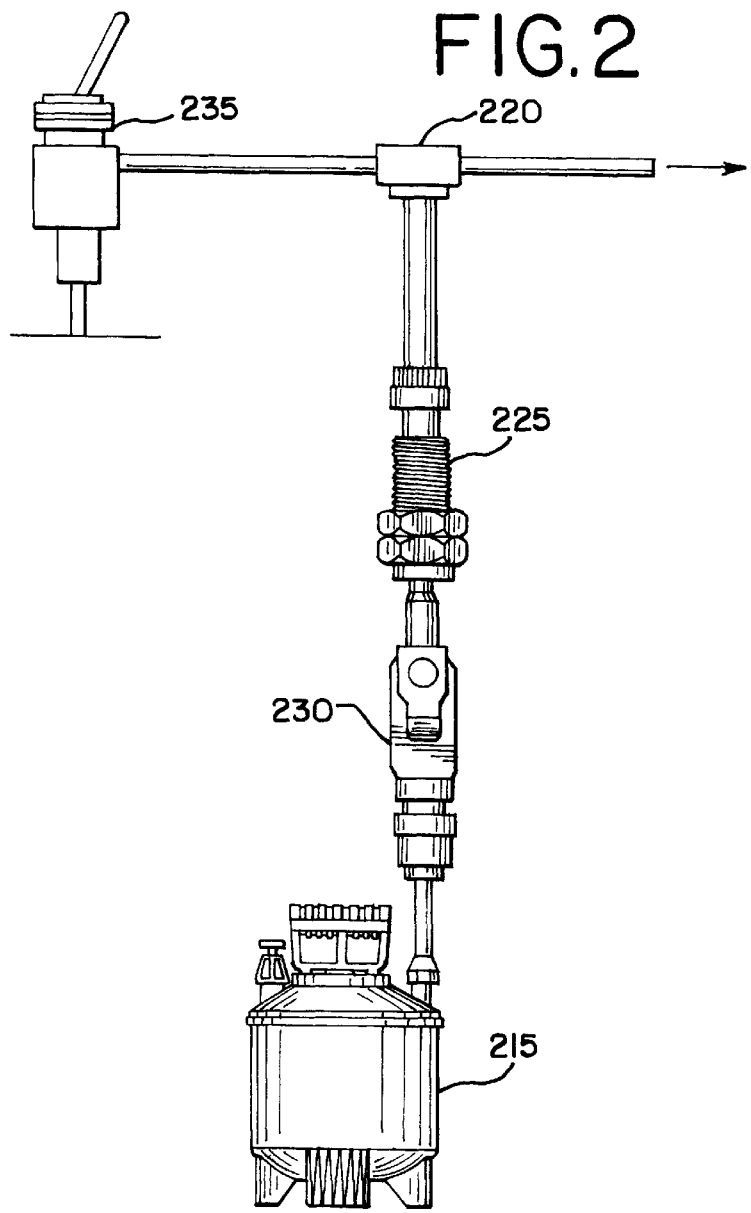
FIG. 2 illustrates a hardware implementation of the first embodiment.

The concepts and processes illustrated may be implemented through hardware, software, and logic circuitry. As shown in FIG. 2, the embodiments may be practiced using a Suncast tank sprayer 215, a ¼" male inline shutoff, a ⅜"×⅜" poly compression union 220, a ¼" female panel mount and a toggle style on/off volume control 235 available from hardware supply outlets and American Dental Accessories. The disclosed embodiments enjoy utility in any dental operatory.

Variations and modifications of the embodiments disclosed herein may be made without departing from scope and spirit of the invention. The aforementioned description is intended to be illustrative rather than limiting and it is understood that the scope of the invention is set forth by the following claims.

I claim:

1. A portable system for descaling and disinfecting dental waterlines for supplying water to a dental unit, said system comprising:

means for defining a portable reservoir adapted to receive a descaling agent and an anti-microbial agent;

quick release means for releasably connecting said reservoir to a dental waterline such that one of said agents flows from said portable reservoir through a plurality of dental waterlines when said means for connecting is engaged while blocking water flow through said waterline during said engagement; and manual means for moving said agents from said portable reservoir through said waterlines directly connected to said reservoir means;

wherein said waterlines furnish water for patient consumption through a dental unit.

2. The portable system according to claim 1, wherein said system further includes a switch for blocking water flow to said dental waterlines.

3. The portable system according to claim 1, wherein said means for moving said agent is a manual pump.

4. The portable system according to claim 1 further including a means for defining a first chamber adapted to receive a descaling agent and a second chamber adapted to receive an anti-microbial agent in said portable reservoir.

5. The portable system according to claim 4, wherein said system further includes a controller for automatically flushing said waterlines first with a descaling agent for a predetermined period of time sufficient to remove scale deposits from said lines, second with a anti-microbial agent for a predetermined period of time sufficient to disinfect said waterlines, and third with a pressurized supply of water for a predetermined period of time sufficient to remove said descaling and anti-microbial agents.

6. A portable system for neutralizing calcium, magnesium, and pathogenic contaminants in a dental unit having at least one waterline, said portable system comprising:
 a water reservoir having sufficient volume to deliver a supply of water to said waterline;
 a routing valve having an outlet secured to said waterline and at least one inlet, wherein said routing valve blocks said supply of water to said waterline when said inlet is selected;
 a portable reservoir having a first chamber adapted to deliver a supply of descaling agent and a second chamber adapted to deliver a supply of anti-microbial agent;
 a quick release connector releasably interconnecting said portable reservoir with said routing valve such that said portable reservoir may be mechanically disconnected from said routing valve without releasing fluid from said waterline;
 a controller operably coupled to said routing valve to control fluid flow through said waterline by selecting one of said anti-microbial agent, descaling agent, and water; and
 a manual pump directly connected to said portable reservoir;
 wherein said waterline furnishes water for patient consumption through a dental unit.

7. The portable system for neutralizing calcium, magnesium, and pathogen contaminants of claim 6, wherein said system is a fully integrated stand-alone device.

8. The portable system for neutralizing calcium, magnesium, and pathogen contaminants of claim 6, wherein said controller is responsive to manual control.

9. The portable system for neutralizing calcium, magnesium, and pathogen contaminants of claim 6, wherein said routing valve is releasably connected to said inlet.

10. The portable system for neutralizing calcium, magnesium, and pathogen contaminants of claim 6, wherein said reservoirs are fully enclosed and subject to substantially constant pressure.

11. The portable system for neutralizing calcium, magnesium, and pathogen contaminants of claim 6, wherein said anti-microbial agent is selected from a group consisting essentially of: lactic acid, tartaric acid, acetic acid, citric acid, ascorbic acid, malic acid, succinic acid, gluconic acid, fumaric acid, and phytic acid.

12. The portable system for neutralizing calcium, magnesium, and pathogen contaminants of claim 11, wherein said anti-microbial agent is combined with an agent selected from a group consisting essentially of: phosphoric acid, nitric acid, sulfuric acid, hydrochloric acid, and alcohol.

13. A transportable water descaling and disinfecting device for treating dental waterlines, comprising:
 a plurality of dental waterlines that furnish water for patient consumption fluidly joined to a water reservoir through a switch that controls water flow;
 a removable fluid reservoir capable of dispensing at least a descaling and a antimicrobial agent;
 a manual pump directly secured to said fluid reservoir and having at least an inlet line connected to said fluid reservoir and an outlet line; and
 a routing valve including a quick release connector adapted to releasably interconnect at least one of said dental waterlines and said outlet line such that said outlet line may be mechanically disconnected from said routing valve without releasing fluid from said dental waterlines.

14. The transportable water descaling and disinfecting device of claim 13, wherein said routing valve comprises a disconnecting coupling.

15. A process for periodically descaling and disinfecting dental waterlines using a portable system, comprising the steps of:
 adapting a valve to releasably interconnect at least one of said waterlines with a reservoir directly connected to a manual pump capable of dispensing at least a descaling agent and a anti-microbial agent through said waterlines through a quick release connector that may be mechanically disconnected from said waterlines without releasing fluid from said waterlines;
 descaling said waterlines by:
  supplying said descaling agent of sufficient volume to said waterlines for a planned period of time sufficient to remove scale deposits from said waterlines;
  flushing said waterlines by draining said descaling agent from said waterlines and rinsing said waterlines with a sufficient volume of pressurized water to flush said descaling agent and said scale deposits from said waterlines;
 disinfecting said waterlines by:
  supplying a anti-microbial agent of sufficient volume to fill said waterlines for a planned period of time sufficient to disinfect said waterlines; and then
  flushing said waterlines by draining said anti-microbial agent from said waterlines and rinsing said waterlines with a pressurized source of water to flush said anti-microbial agent from said waterlines;
  wherein said waterlines furnishes water for patient consumption through a dental unit.

16. The process for periodically descaling and disinfecting dental waterlines of claim 15, wherein said process is repeated.

17. The process for periodically descaling and disinfecting dental waterlines of claim 15, wherein said pressurized water is softened before flushing said waterlines.

* * * * *